US00PP08932P

United States Patent [19]

Bradford et al.

[11] Patent Number: Plant 8,932

[45] Date of Patent: Oct. 11, 1994

[54] APRICOT TREE (GOLDENSWEET)

[76] Inventors: Lowell G. Bradford, 12439 E. Savana Rd.; Norman G. Bradford, 11875 E. Savana Rd., both of Le Grand, Calif. 95333

[21] Appl. No.: 185,390

[22] Filed: Jan. 24, 1994

[51] Int. Cl.[5] ..... A01H 5/00
[52] U.S. Cl. ..... Plt./39
[58] Field of Search ..... Plt. 39

*Primary Examiner*—James R. Feyrer

[57] ABSTRACT

The present invention relates to an apricot tree and more particularly to a new and distinct variety broadly characterized by a medium size, vigorous, self-fertile and very productive tree. The fruit matures under the ecological conditions described in mid June, with first picking on Jun. 9, 1993, and is uniformly medium in size, freestone in type, light orange in skin color, attractive in shape, deliciously sweet in flavor, and exceptionally firm in texture, resulting in excellent quality for shipping and storage. The variety was developed as an open pollinated seedling of an unnamed self-sterile seedling.

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of apricot tree, which has been denominated varietally as "Goldensweet". Each year we grow a large number of seeds from selected seed parents that have been hybridized by selected pollen parents. We also grow a large number of seeds from selected seed parents that were open pollinated by unknown pollen sources. The present variety was developed by us in 1985, and the resulting seedling was planted in a cultivated area of our experimental orchard at Bradford Farms near Le Grand, Calif. in Merced County (San Joaquin Valley). Specifically, this seedling was originated by growing an open pollinated seed of an unnamed self-sterile seedling. Subsequent to origination of the present variety of apricot tree, we asexually reproduced it by budding and grafting, and such reproduction of plant and fruit characteristics were true to the original plant in all respects.

The present variety is most similar to the Patterson U.S. Plant Pat. No. 2,877) apricot by being self-fertile and by producing fruit that is medium in size, orange in color, and firm in texture, but is distinguished therefrom and an improvement thereon by blooming about 7 days later and by producing fruit that is much sweeter in flavor and that matures about seven days earlier.

DRAWING

The accompanying photograph exhibits four whole fruits positioned to display the characteristics of the skin color and form; one fruit divided along the structure to reveal the flesh, stone, and stone cavity; and several leaves, all typical of the subject variety.

POMOLOGICAL CHARACTERISTICS

Referring now more specifically to the pomological characteristics of this new and distinct variety of apricot tree, the following has been observed under the ecological conditions prevailing at the experimental orchard of the inventors near Le Grand, Merced County (San Joaquin Valley), Calif., and was developed at the state of hard eating ripe on Jun. 14, 1994. All major color code designations are by reference to the Inter-Society Color Council, National Bureau of Standards. Common color names are also used occasionally.

TREE

Size: Medium.
Vigor: Vigorous.
Growth: Spreading and dense.
Form: Round topped.
Hardiness: Hardy.
Production: Very productive.
Bearing: Regular bearer.
Trunk:
- *Size.*—Medium.
- *Texture.*—Shaggy.
- *Bark color.*—Grayish brown [61. gy.Br].
- *Lenticels.*—Numerous. Color: Brownish gray [64. brGy]. Size: $\frac{1}{8}$" to $\frac{3}{8}$"[3.2–9.5 mm.].

Branches:
- *Size.*—Medium.
- *Texture.*—Medium.
- *Color.*—1st year wood topside: Very dark purplish red [260. v.d.pR]. 1st year wood underside: Moderate yellow green [120. m.YG]. Older wood: Grayish brown [61. gy.Br].
- *Lenticels.*—Numerous, medium.

Leaves:
- *Size.*—Medium. Average length: $2\frac{7}{8}$" [73.0 mm.]. Average width: 2 11/16" [68.3 mm.].
- *Thickness.*—Medium.
- *Form.*—Orbicular
- *Apex.*—Slightly mucronate.
- *Base.*—Cordate.
- *Surface.*—Smooth.
- *Color.*—Dorsal Surface: Moderate olive green [125. m.OlG]. Venral Surface: Moderate yellow green [120. m.YG].
- *Margin.*—Finely serrate.
- *Venation.*—Pinnately net veined.
- *Petiole.*—Average length: $1\frac{1}{8}$" [28.6 mm.]. Average thickness: 3/64" [1.2 mm.]. Dorsal color: Moderate reddish brown [43. m.rBr]. Ventral color: Brilliant yellow green [116. brill.YG].
- *Stipules.*—Few. Average Length: 3/16" [4.8 mm.].
- *Glands.*—Average Number: 6 per leaf. Position: Mostly oppositely positioned on petiole. Size:

Small. Form: Globose. Color: Moderate reddish brown [43. m.rBr].

Flower buds:

*Hardiness.*—Hardy.

*Size.*—Medium.

*Length.*—Medium.

*Form.*—Free.

*Surface.*—Pubescent.

Flowers:

Blooming period.—Late as compared with other varieties.

Size.—Medium.

Color.—White [263. White].

FRUIT

Maturity when described: Firm but eating ripe, Jun. 14, 1993.

Date of first picking: Jun. 9, 1993.

Date of last picking: Jun. 22, 1993.

Size: Uniform, medium.

*Average diameter axially.*—2" [50.8 mm].

*Average traversely in suture plane.*—2"[50.8 mm].

Form: Uniform, symmetrical, globose, but compressed laterally.

*Longitudinal section form.*—Round.

*Transverse section through diameter.*—Elliptical.

Suture: Sharply creased near the base, an inconspicuous line toward the apex, discontinuing at the pistil point.

Ventral surface: Rounded.

Lips: Lipped throughout on one side, slightly unequal.

Cavity: Flaring, elongated in the suture plane with suture showing on both sides.

Base: Slightly cuneate, slightly truncate.

Apex: Rounded and truncate, a few having a slight pin-hole at the tip.

Pistil point: Negligibel in length.

Stem: Medium.

*Average length.*—¼" [6.4 mm.].

*Average width.*—3/32" [2.4 mm.].

Skin:

*Thickness.*—Medium.

*Texture.*—Medium.

*Tenacity.*—Tenacious to flesh.

*Tendency to crack.*—Some in wet season.

*Color.*—Light orange [52. 1.0] with some strong reddish orange [35. s.rO] blushing in sunlight.

Flesh:

*Color.*—Strong orange [50 s.O].

*Amygdalin.*—Scarce.

*Juice.*—Abundant, rich.

*Texture.*—Firm, tough, meaty.

*Fibers.*—Abundant, fine, tender.

*Ripens.*—Evenly, but slightly earlier at the apex.

*Flavor.*—Excellent blend of sugar and acid.

*Aroma.*—Medium.

*Eating quality.*—Very best.

*Brix.*—17 to 22.

*Fresh to dry ratio.*—4.6 to 1.

STONE

Type: Freestone.

Form: Oval.

Base: Straight.

Apex: Rounded.

Sides: Equal.

Surface: Somewhat rough, no pitting or furrowing, one ridge on each side of the dorsal fin.

Color: Moderate yellowish brown [77. m.yBr].

Average pit wall thickness: 5/64" [2.0 mm.].

Tendency to split: None observed.

Kernel:

*Form.*—Obovoid.

*Taste.*—Bitter.

*Viable.*—Yes.

*Average width.*—½" [12.7 mm.].

*Average length.*—11/16" [17.5 mm.].

Pellicle color: Grayish yellowish brown [80. gy.yBr], light orange yellow [70.1.OY]when dry.

Amygdalin: Abundant.

USE

Market: Fresh market, long distance shipping, drying, and freezing.

Keeping quality: Excellent.

Shipping quality: Excellent.

Resistance to insects: No unusual susceptibiliites noted.

Resistance to diseases: No unusual susceptibilities noted.

Although the new variety of apricot tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of apricot tree, substantially as illustrated and described, which most nearly resembles the Patterson apricot (U.S. Plant Pat. No. 2,877) by being self-fertile and by producing fruit that is medium in size, orange in color, and firm in texture, but is distinguished therefrom and an improvement thereon by blooming about 7 days later and by producing fruit that matures about seven days earlier and is much sweeter in flavor.

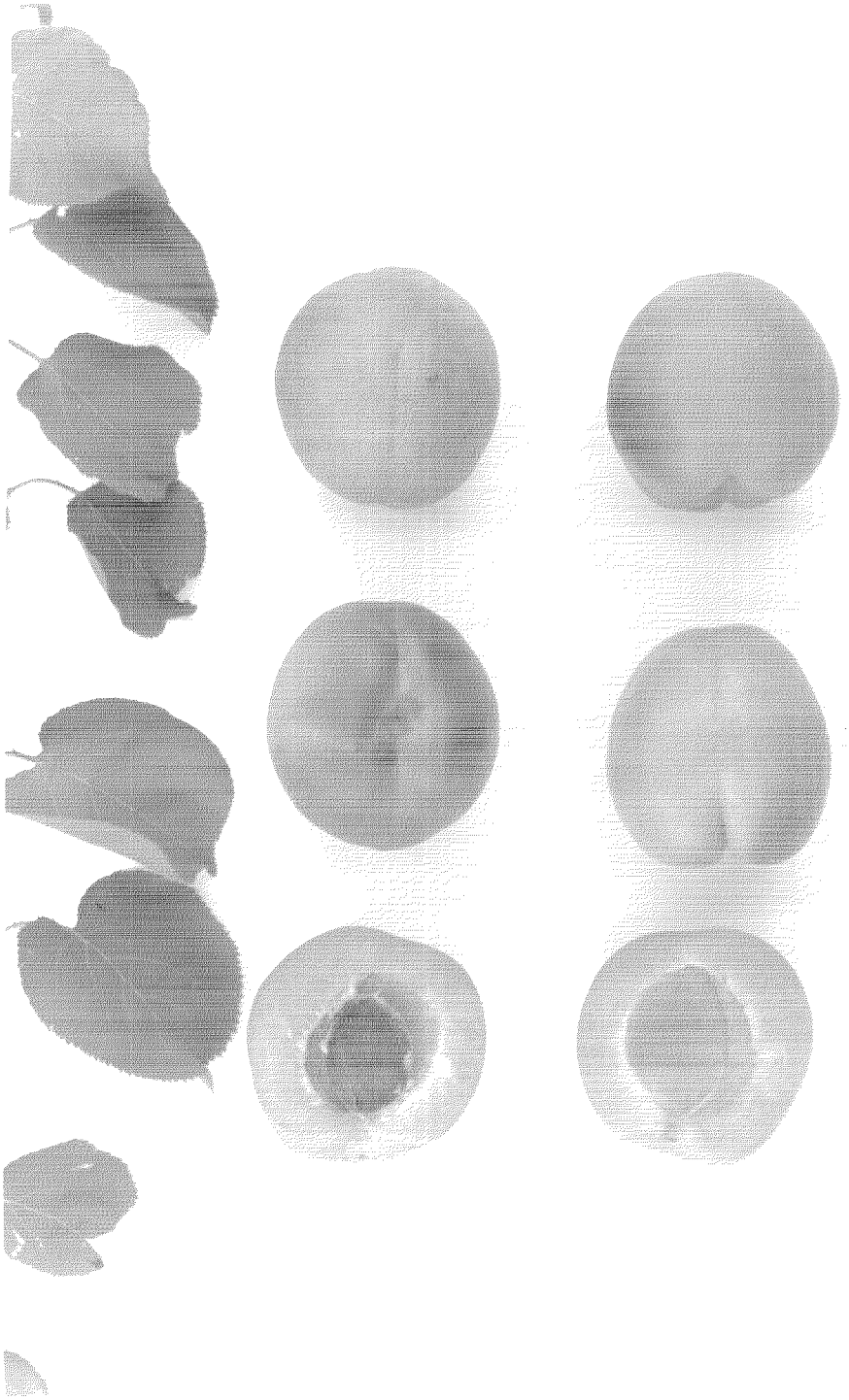

* * * * *